United States Patent
Driebe et al.

(10) Patent No.: US 9,914,978 B2
(45) Date of Patent: Mar. 13, 2018

(54) METHODS, KITS, AND COMPOSITIONS USEFUL IN SELECTING AN ANTIBIOTIC TO TREAT MRSA

(75) Inventors: Elizabeth Driebe, Flagstaff, AZ (US); David Engelthaler, Flagstaff, AZ (US); Jolene Bowers, Flagstaff, AZ (US); Paul Keim, Flagstaff, AZ (US)

(73) Assignees: The Translational Genomics Research Institute, Phoenix, AZ (US); Arizona Board of Regents on Behalf of Northern Arizona University, Flagstaff, AZ (US)

( * ) Notice: Subject to any disclaimer, the term of this patent is extended or adjusted under 35 U.S.C. 154(b) by 1725 days.

(21) Appl. No.: 13/051,780

(22) Filed: Mar. 18, 2011

(65) Prior Publication Data
US 2011/0230363 A1 Sep. 22, 2011

Related U.S. Application Data

(63) Continuation of application No. 61/315,676, filed on Mar. 19, 2010.

(60) Provisional application No. 61/432,511, filed on Jan. 13, 2011.

(51) Int. Cl.
*C12Q 1/68* (2006.01)
*C07H 21/04* (2006.01)
*C12M 1/34* (2006.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS 6,773,882 B2 * 8/2004 Hogan ............... C12Q 1/6895
435/471
2003/0049636 A1 3/2003 Bergeron et al.

FOREIGN PATENT DOCUMENTS

WO WO2009042851 4/2009

OTHER PUBLICATIONS

Gomaa et al. (Egyptian Journal of Medical Microbiology Oct. 2006 vol. 15 p. 763).*
Sinsimer et al. (Journal of Clinical Microbiology 2005 vol. 43 p. 4585).*
Diffenbach (PCR methods and Applications (1993) vol. 3, pp. S30-S37).*
Roux et al (PCR Methods and Applications (1995) vol. 4, pp. s185-s194).*
International Preliminary Report on Patentability for PCT Application NO. PCT/US2011/029048 dated Sep. 25, 2012.
International Search Report and Written Opinion for PCT Application No. PCT/US2011/029048 dated Aug. 9, 2011.
Patel. et al, "Multiplex PCR detection of vanA, vanB, vanC-1, and vanC-2/3 genes in enterococci" J. Clin. Microbiol. Mar. 1997 vol. 35, No. 3, pp. 703-707.
Whitener et al. "Vancornycin-resistant *Staphylococcus aureus* in the absence of vancomycin exposure" Clin. Infect. Dis. Apr. 15, 2004 vol. 38 No. 8 pp. 1049-1055.
Roger et al. "Evaluation of a vanA-specific PCR assay for detection of vancomycin-resistant Enterococcus faecium during a hospital outbreak" J. Clin. Microbiol. Oct. 1999 vol. 37 No. 10 pp. 3348-3349.
Ghidan et al. "PCR detection of the vanA gene in a vancomycin-resistant Enterococcus faecalis clinical isolate from Hungary" J. Antimicrob. Chemother. (2000) vol. 46 pp. 323-342.

* cited by examiner

*Primary Examiner* — Katherine D Salmon

(57) ABSTRACT

The present invention provides a method, a kit and composition for determining MRSA and other *Staphylococcus* strain resistance to one or more antibiotic agents through detecting the presence of the respective antibiotic resistance gene. The methods include real-time PCR assays, and the kits and compositions include oligonucleotides used as primers and probes.

15 Claims, No Drawings

METHODS, KITS, AND COMPOSITIONS USEFUL IN SELECTING AN ANTIBIOTIC TO TREAT MRSA

CROSS-REFERENCE TO RELATED APPLICATIONS

This application claims the priority of U.S. provisional applications entitled METHODS, KITS, AND COMPOSITIONS USEFUL IN SELECTING AN ANTIBIOTIC TO TREAT MRSA, with application No. 61/315,676, filed on Mar. 19, 2010, which is hereby incorporated by reference in its entirety. This application also cross reference to U.S. provisional application entitled METHODS, KITS AND COMPOSITIONS FOR DETECTION OF MRSA, with application No. 61/432,511, filed on Jan. 13, 2011, which is hereby incorporated by reference in its entirety.

STATEMENT REGARDING FEDERALLY SPONSORED RESEARCH

This invention was made with government support under Al066581 awarded by the National Institutes of Health. The government has certain rights in this invention.

FIELD OF THE INVENTION

The present invention generally provides methods, kits and compositions to identify the presence of antibiotic resistance genes in a sample. More particularly, the present invention provides assays based on identified gene sequences, primers and probes designed accordingly to provide an antibiotic resistance profile for MRSA and other strains of *Staphylococcus*, including MRSA, MSSA, MRCNS and MSCNS.

BACKGROUND OF THE INVENTION

Methicillin-resistant *Staphylococcus aureus* (MRSA) has become one of the most dangerous infectious agents in the U.S. and elsewhere, with a higher mortality rate than HIV-AIDS. MRSA is a strain of *Staphylococcus aureus* (*S. aureus*) bacteria, a common type of bacteria that may live on the skin and in the nasal passages of healthy people. MRSA does not respond to some of the antibiotics generally used to treat staphylococcal and other bacterial infections. MRSA is also called multidrug-resistant *Staphylococcus aureus*.

Healthcare-associated MRSA (HA-MRSA) infections occur in people who are or have recently been in a hospital or other health-care facility. Many people may be at risk of MRSA infection due to receiving healthcare services in an environment where the MRSA bacteria are colonized on surfaces, healthcare workers, the patient or other patients. Community-associated MRSA (CA-MRSA) infections occur in otherwise healthy people who have not recently been in the hospital. In fact, MRSA has become a primary cause of skin and soft tissue infections among persons without extensive exposure to healthcare settings, and the outbreaks have occurred in athletic team facilities, correctional facilities, and military basic training camps.

HA-MRSA and CA-MRSA typically have differing antibiotic resistance patterns, requiring extensive susceptibility testing to identify appropriate treatment regimens for each case. In addition to methicillin-sensitive *S. aureus* (MSSA) and methicillin-resistant *S. aureus* (MRSA) strains, there are CNS, or CoNS, (coagulase-negative staphylococci) species, close relatives of the bacterium *Staphylococcus aureus*, commonly found in humans. Many strains of CNS are also resistant to methicillin (MRCNS) using a similar SCCmec gene cassette mechanism as MRSA. Specifically, methicillin-resistant *S. epidermidis* (MRSE) is the strain in the CNS species most commonly seen among MRCNS carriers. Among immunocompromised patients, MRCNS, especially MRSE, can lead to infections and is common cause of wound, blood, and respiratory infections. MRSE can cause severe infections in immune-suppressed patients and those with central venous catheters.

Because of MRSA's resistance to multiple antibiotics, new and broad-spectrum antibiotics are often deployed against MRSA, for example, vancomycin, aminoglycoside, penicillin, macrolide, tetracycline and other antibiotics are the alternatives for MRSA treatment. However, MRSA has a potential to develop resistance to antibiotics to which it once was susceptible. Therefore, a rapid, accurate, sensitive and efficient method of determining the evolved antimicrobial resistance for *Staphylococcus* strains including MRSA, MSSA, MRCNS and MSCNS is greatly needed, so that an antibiotic will not be prescribed for infection treatment if the strain has already acquired resistance to the antibiotic agent that once was effective.

SUMMARY OF THE INVENTION

Briefly, therefore, one aspect of the present invention provides a profiling assay for determining a *Staphylococcus* strain's resistance to one or more antibiotic agents. The profiling assay comprises one or more individual assays chosen from vanA assay, aacA assay, blaZ assay, ermA assay, ermC assay, tetK assay, tetM assay and msrA assay. Each of the above assays detects the presence of a specific targeted sequence chosen from vanA gene, aacA gene, blaZ gene, ermA gene, ermC gene, tetK gene, tetM gene and msrA gene, respectively. The *Staphylococcus* strain for resistance profiling may be a MRSA, MSSA, MRSE, MSSE, or other *Staphylococcus* strain.

Another aspect of the present invention provides a method for determining a *Staphylococcus* strain's resistance to one or more antibiotic agents. The method comprises (1) receiving a sample; and (2) detecting presence of one or more antibiotic resistance genes by applying one or more assays to the sample, the assay being chosen from vanA assay, aacA assay, blaZ assay, ermA assay, ermC assay, tetK assay, tetM assay, and msrA assay.

A further aspect of the invention encompasses a kit for determining a *Staphylococcus* strain's resistance to one or more antibiotic agents. The kit comprises one or more primer sets and probes for assays chosen from vanA assay, aacA assay, blaZ assay, ermA assay, ermC assay, tetK assay and tetM assay. The kit may be used to a *Staphylococcus* strain that is a MRSA, MSSA, MRSE, MSSE, or other *Staphylococcus* strain.

Other aspects and iterations of the invention are described in more detail below.

DETAILED DESCRIPTION OF THE INVENTION

The present invention discloses assays, methods and kits designed to detect resistance of MRSA, MSSA, MRCNS, MSCNS and other *Staphylococcus* strains to antibiotic agents, which include vancomycin, aminoglycoside, penicillin, macrolide and tetracycline.

It is known that bacterial strains can evolve mechanisms to inhibit the action of an agent it once responded to. There are different mechanisms leading to bacterial resistance including but not limited to enzyme modification, ribosomal mutations, activated efflux of the drug out of the bacteria, and acquisition of antibiotic resistance genes. For example, Staphylococcal resistance to penicillin is mediated by penicillinase (a form of β-lactamase) production: an enzyme that cleaves the β-lactam ring of the penicillin molecule, rendering the antibiotic ineffective. In another example, resistance to methicillin is conferred by the mecA gene, which codes for an altered penicillin-binding protein that has a lower affinity for binding β-lactams. The lowered affinity for β-lactam binding leads to resistance to all β-lactam antibiotics, such as penicillins, cephalosporins, and carbapenems. Bacterial resistance to an antibiotic may be due to one, two, or more mechanisms. Understanding the resistance mechanism and developing relevant assays to determine an evolved resistance of *Staphylococcus* strains including MRSA, MSSA, MRCNS and MSCNS is one aspect of the present invention.

(I) Antibiotic Resistance or Susceptibility in MRSA and Other Species or Strains (a) Molecules for Determining Susceptibility of MRSA to Certain Antibiotic Agent In addition to methicillin-resistant *S. aureus* (MRSA), methicillin-resistant *S. epidermidis* (MRSE) leads to infections among immunocompromised patients. Therefore, both MRSA and MRSE are of great concern and anti-MRSA or MRSE agents, such as antibiotics are needed. Utilizing various resistance gene sequences, alleles of those sequences, or biomarkers derived from transcriptional or translational products of the resistance genes and their alleles enables rapid an accurate determination of appropriate anti-MRSA or MRSE agents.

(i) Antibiotic Resistance Genes Sequences

There are different mechanisms leading to bacterial resistance. The presence of an antibiotic resistance gene sequence in a species or strain is one of the mechanisms that can be useful in determining its susceptibility or resistance phenotype to particular antibiotic agents. In a small number of cases, carrying an antibiotic resistance gene may still confer susceptibility to that antibiotic. However, if a particular antibiotic resistance gene or alleles thereof is present in a bacterium, the bacterium can be determined to be resistant to the antibiotic with a high confidence.

When a particular antibiotic resistance gene sequence conferring antibiotic resistance of a strain is identified, probes or primers may be designed based on any part of the sequence. The probes or primers may also be the entirety of the sequence. The primers or probes designed according to particular species or strain sequence may also be represented in degenerate form, or comprising chemically modified nucleic acids, or any other components that facilitates the detection of the identifying sequence of a strain or species. The concept of a sequence identified to be specific to a species or strain further encompasses nucleic acid sequences that are less than 100% identical to the specific sequence but are still capable of specifically detecting the species or strain. Note that in a nucleic acid sequence, T or U may be used interchangeably depending on whether the nucleic acid is DNA or RNA. A sequence having less than 60% 70%, 80%, 90%, 95%, 99% or 100% identity to the identifying sequence may still be encompassed by the invention if it is able of binding to its complimentary sequence and/or facilitating nucleic acid amplification of a desired target sequence. The primers or probes designed according to particular species or strain sequence may also be represented in degenerate form, or comprising chemically modified nucleic acids, or any other components that facilitate the identification of the identifying sequence of a strain or species.

Identifying antibiotic resistance gene sequences and developing the probes or primers to detect the presence of those sequences to determine resistance to certain antibiotic agents of MRSA, MRSE, other *Staphylococcus* strains, or even other pathogens, are disclosed herein. One aspect of the present invention discloses that vanA gene can be used to detect glycopeptides resistance of a *S. aureus*. The presence of vanA gene indicates that the *S. aureus* is resistant to vancomycin, whereas the absence of vanA gene indicates that the *S. aureus* is highly likely susceptible to vancomycin, a glycopeptides antibiotic. One aspect of the present invention discloses that aacA gene can be used to detect aminoglycoside resistance of a *S. aureus*. The presence of aacA gene indicates that the *S. aureus* is resistant to aminoglycoside, whereas the absence of aacA gene indicates that the *S. aureus* is highly likely susceptible to aminoglycoside. Another aspect of the present invention discloses that the blaZ genes can be used to detect penicillin resistance of a *S. aureus*. The presence of blaZ genes indicates that the *S. aureus* is highly likely resistant to penicillin. Yet another aspect of the present invention discloses that the ermA and ermC genes can be used to specifically detect macrolide resistance of a *S. aureus*. The presence of ermA indicates the *S. aureus* is highly likely resistant to macrolide. A further aspect of the present invention discloses that the tetK gene and tetM gene can be used to specifically determine tetracycline susceptibility of a *S. aureus*. The presence of tetM indicates a high likelihood of susceptibility, and the absence of both tetK and tetM indicates the *S. aureus* is most likely susceptible to tetracycline. Yet, another aspect of the present invention discloses that the msrA gene can be used to specifically determine macrolide resistance of a *S. aureus*. The presence of msrA indicates that the *S. aureus* is resistant to macrolide.

(ii) Alleles of Antibiotic Resistance Genes

Identifying alleles to a sequence specific to resistance of a *S. aureus* to certain antibiotic agents is another aspect of this invention. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spacial expression specificity. The presence of an allele may be detected through the use of any process known in the art, including using primers and probes designed accordingly for PCR, sequencing, hybridization analyses. An allele may also be called a mutation or a mutant. An allele may be compared to another allele that may be termed a wild type form of an allele. In some cases, the wild type allele is more common than the mutant.

One aspect of the present invention provides that vanA gene alleles may be used to specifically detect glycopeptides resistance of a *S. aureus*. One aspect of the present invention provides that aacA gene alleles may also be used to specifically detect aminoglycoside resistance of a *S. aureus*. Another aspect of the present invention provides that the blaZ genes may be used to specifically detect aminoglycoside resistance of a *S. aureus*. Yet another aspect of the present invention provides that the ermA and ermC gene alleles may be used to specifically detect macrolide resistance of a *S. aureus*. A further aspect of the present invention provides that the tetK and tetM gene alleles can be used to specifically determine tetracycline resistance of a *S. aureus*. Yet another aspect of the present invention provides that the msrA gene alleles can be used to specifically determine macrolide resistance of a *S. aureus*. Additional sequences to detect these above mentioned genes are in Example 2 and the sequence listing.

(iii) Biomarkers Indicating the Presence of a Resistance Gene

Molecules, including but not limited to small RNAs, peptides and proteins, derived from transcription or translation process of the resistance gene nucleic acid sequences and alleles thereof may serve as biomarkers indicating the agent resistance or susceptibility phenotype of a *S. aureus*. Methods of detecting a biomarker generally involve assessing the expression of material created from a genomic DNA template such as a RNA or protein molecule. Such expression may be assessed by any of a number of methods used currently in the art and yet to be developed.

Once resistance specific genes, alleles thereof, or other nucleic acid based biomarkers thereof are identified, primers and probes may be designed to screen samples to specifically and selectively detect the presence of these genes, alleles or biomarkers, and therefore the resistance or susceptibility to a particular agent of a *S. aureus* may be determined through various methods including PCR-based methods such as real-time PCR, quantitative PCR, quantitative real time PCR; allele specific ligation; comparative genomic hybridization; sequencing; and other methods known in the art. One aspect of the invention provides multiplex RT-PCR assays combining various individual assays that comprise specific primer sets and probes depending on the application to detect antibiotic agent resistance of a *S. aureus*.

As to probes, they may be used for single probe analysis or multiplex probe/primers combined RT-PCR/PCR analysis. Oligonucleotide probes complimentary to a selected sequence within the target sequence may be designed. In one exemplary example, oligonucleotide probes facilitating RT-PCR/PCR product detection are complimentary to a selected sequence within the target sequence downstream from either the upstream or downstream primer, therefore these probes hybridize to an internal sequence of the amplified fragment of a targeted sequence.

The concept of oligonucleotides includes any DNA or RNA molecule of two or more nucleotides, whether from a natural source, artificially synthesized, or produced through the use of recombinant DNA technology. A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide sequence. The length of the oligonucleotide depends on how the oligonucleotide will be used. One skilled in the art would understand the approximate length of oligonucleotide necessary in any given method. Depending on the method, an oligonucleotide may be 0 to 1000 bases in length. In other aspects, it may be 5 to 500 bases in length, 5 to 100 bases in length, 5 to 50 bases in length, or 10 to 30 bases in length. The primers or probes designed according to particular species or strain sequence may also be represented in degenerate form, or comprising chemically modified nucleic acids, or any other components that facilitates the identification of the identifying sequence of a strain or species. An oligonucleotide may be in any physical formulation including as a solid (including crystal salts as necessary,) or it may be in a solution such as in a buffered solution.

(b) Samples Known or Determined to Contain MRSA or Other *Staphylococcus* Strains Samples often come with a mixture of bacteria species. In addition to MSSA and MRSA, there are CNS, or CoNS, which include other commercial and clinically important *Staphylococcus* species. Multiplex assays utilizing prime sets and/or probes, methods and kits designed to differentiate among MSSA, MRSA, MRCNS and MSCNS, including the MRSE and MSSE of the CNS species, in a sample suspected of carrying these species were disclosed in U.S. provisional application 61/432,511. Samples may be suspected of containing a bacterium if they are derived from a subject displaying symptoms of a bacterial infection or from an environmental sample from an area in which a bacterium is thought to be endemic or from a subject recently present in a hospital or other environment found to contain MRSA or MRSE. A subject may display signs or symptoms of MRSA infection, which include red, swollen and painful areas on the skin, drainage of pus or other fluids from the site, fever, skin abscesses, warmth around the infected area, chest pain, chills, cough, fatigue, malaise, headache, muscle ache, rash, and shortness of breath.

A sample may be derived from anywhere that a bacterium or any part of a bacterium may be found, including but not limited to soil, air, water, solid surfaces (whether natural or artificial,) culture media, foodstuffs. Additionally, a sample may be derived from a subject, from agricultural, environmental, or any and all other sources.

A subject may be any organism that may be infected by a bacterium, such as plants; animals, including but not limited to humans, companion animals such as dogs, cats, birds, or small mammals, livestock animals such as cattle, pigs, sheep, poultry and any other domesticated or wild animal. Samples derived from subjects include, but are not limited to, a collection of nucleic acids in all forms, biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample such as peripheral blood, lymph fluid, ascites, serous fluid, pleural effusion, sputum, bronchial wash, bronchioalveolar lavage fluid (BALF), cerebrospinal fluid, semen, amniotic fluid, lacrimal fluid, stool, urine, hair, or any other source in which a bacterium, or any part of a bacterium, might be present.

Samples may be collected by any and all methods now known or yet to be disclosed, including swiping or swabbing an area or orifice, removal of a piece of tissue as in a biopsy, any method known to collect bodily fluids, wiping down a surface, collecting a sample of liquid, collecting an air sample, or any other method that may be used to collect bacteria in such a way as to preserve biological material such as DNA, RNA or protein for analysis.

The determination whether the *S. aureus* strain in a sample carries the resistance to an antibiotic agent in the present invention depends on detecting the presence of the agent resistance gene, or alleles and biomarker thereof, in the *S. aureus* contained in a sample. The nucleic acids of the resistance gene or alleles may include, but need not be limited to, RNA, cDNA, tRNA, mitochondrial DNA, plasmid DNA, siRNA, genomic DNA, or any other naturally occurring or artificial nucleic acid molecule originated from a bacterium.

(c) Agent Against MRSA and Other *Staphylococcus* Strains

An agent against MRSA may be an antibiotic agent, a pharmaceutically active ingredient or acceptable salt thereof, a drug, a chemical, an antibody, or a virus.

An antibiotic agent is any composition that limits the growth of bacteria up to and including killing the bacteria. Examples of antibiotics include, but need not be limited to, aminoglycosides such as amikacin, gentamicin, kanamycin, neomycin, netilmicin, streptomycin, tobramycin, and paromomycin; ansamycins such as geldanamycin and herbimicin; carbacephems such as loracarbef; carbapenems such as ertapenem, doripenem, imipenem, cilastatin and meropenem; cephalosporins such as cefadroxil, cefazolin, cefalothin, cefalexin, cefaclor, cefamandole, ceofoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime and ceftobiprole; glycopeptides such as teicoplanin, vancomycin, and telavancin; macrolides such as azithromycin, clarithromycin, dirithromycin, erythromycin, roxithromycin, troleandomycin, telithromycin, and spectinomycin; monobactams such as aztreonam; penicillins such as amoxicillin, ampicillin azlocillin, carbenicillin, cloxacillin, dicloxacillin, flucloxacillin, mezlocillin, meticillin, nafcillin, oxacillin, penicillin, piperacillin, and ticarcillin; polypeptides such as bacitracin, colistin, and polymyxin B; quinolones such as ciproflaxin, enoxacin, gatifloxacin, levofloxacin, lomefloxacin, norfloxacin, ofloxacin, trovafloxacin, grepafloxacin, sparfloxacin, and temafloxacin; sulfonamides such as mafenide, sulfonamidochysoidine, sulfacetamide, sulfadiazine, sulfamethizole, sulfanilamide, sulfasalazine, sulfisoxazole, trimethoprim, and trimethoprim-sulfamethoxazole; tetracyclines such as demeclocycline, doxycycline, minocycline, oxytetracycline, and tetracycline; or arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin, dalfopristin, rifampicin, thiamphenicol, tinidazole, dapsone, and clofazimine. Antibiotics against MRSA may be any of the known or unknown composition or derivatives thereof. A preferred group of antibiotic agents comprises glycopeptide, aminoglycoside, penicillin, macrolide and tetracycline.

An agent against MRSA and other *Staphylococcus* strains may be a drug, whether it is a pro-drug, activated or metabolized form, consisting of charged, uncharged, hydrophilic, hydrophobic or zwitter-ion species which make their entry by simple diffusion, carrier mediated transport dependent and not dependent on energy requirements.

An agent against MRSA and other *Staphylococcus* strains may be a chemical. The chemical may be industrial chemicals, household chemicals, and other environmental chemicals.

An agent against MRSA and other *Staphylococcus* strains may be an antibody. The term "antibody" is used herein in the broadest sense and refers generally to a molecule that contains at least one antigen binding site that immunospecifically binds to a particular antigen target of interest. Antibody thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term thus includes full length antibodies and/or their variants as well as immunologically active fragments thereof, thus encompassing, antibody fragments capable of binding to a biological molecule (such as an antigen or receptor) or portions thereof, including but not limited to Fab, Fab', F(ab')2, facb, pFc', Fd, Fv or scFv (See, e.g., CURRENT PROTOCOLS IN IMMUNOLOGY, (Colligan et al., eds., John Wiley & Sons, Inc., NY, 1994-2001).

An agent against MRSA and other *Staphylococcus* strains may be a virus, including but not limited to the bacterial virus which has the ability to infect and/or destroy bacteria. The bacterial virus may or may not be species-specific.

(d) Preferred Embodiments

As shown in Table A, in one preferred embodiment of the present invention, primer set 1, represented by SEQ ID NO. 1 and 2, and probe 1, represented by SEQ ID NO. 3, are selective for glycopeptides resistance gene vanA.

In preferred one embodiment, primer set 2, represented by SEQ ID NO. 4 and 5, and probe 2, represented by SEQ ID NO. 6, are selective for aminoglycoside resistance gene aacA.

In one preferred embodiment, primer set 3, represented by SEQ ID NO. 7 and 8, and probe 3, represented by SEQ ID No. 9, are selective for penicillin resistance gene blaZ.

In one preferred embodiment, primer set 4, represented by SEQ ID NO. 10 and 11, and probe 4, represented by SEQ ID No. 12, are selective for macrolide resistance gene ermA.

In one preferred embodiment, primer set 5, represented by SEQ ID NO. 13 and 14, and probe 5, represented by SEQ ID No. 15, are selective for macrolide resistance gene ermC.

In yet another preferred embodiment, primer set 6, represented by SEQ ID NO. 16 and 17, and probe 6, represented by SEQ ID No. 18, are selective for tetracycline resistance gene tetK.

In yet another preferred embodiment, primer set 7, represented by SEQ ID NO. 19 and 20, and probe 7, represented by SEQ ID No. 21, are selective for tetracycline resistance gene tetM.

In still another preferred embodiment, primer set 8, represented by SEQ ID NO. 22 and 23, and probe 8, represented by SEQ ID No. 24, are selective for macrolide resistance gene msrA.

The oligonucleotides for the primers and probes may be chemically synthesized by any of a number of methods including sequential synthesis, solid phase synthesis, or any other synthesis method now known or yet to be disclosed. Alternatively, oligonucleotides may be produced by recombinant DNA based methods.

TABLE A

Assays, Primers and Probes

| Assay | | Description | SEQ ID NO. |
|---|---|---|---|
| vanA | Primer set 1 | vanA_forward | 1 |
| | | vanA_reverse | 2 |
| | Probe 1 | VanA_Probe | 3 |
| aacA | Primer set 2 | aacA forward | 4 |
| | | aacA_reverse | 5 |
| | Probe 2 | aacA_probe | 6 |
| blaZ | Primer set 3 | blaZ_forward | 7 |
| | | blaZ_reverse | 8 |
| | Probe 3 | blaZ_probe | 9 |
| ermA | Primer set 4 | ermA_forward | 10 |
| | | ermA_reverse | 11 |
| | Probe 4 | ermA_probe | 12 |

TABLE A-continued

Assays, Primers and Probes

| Assay | | Description | SEQ ID NO. |
|---|---|---|---|
| ermC | Primer set 5 | ermC_forward | 13 |
| | | ermC_reverse | 14 |
| | Probe 5 | ermC_probe | 15 |
| tetK | Primer set 6 | tetK forward | 16 |
| | | tetK_reverse | 17 |
| | Probe 6 | tetK_Probe | 18 |
| tetM | Primer set 7 | tetM_forward | 19 |
| | | tetM_reverse | 20 |
| | Probe 7 | tetM_probe | 21 |
| msrA | Primer set 8 | msrA_forward | 22 |
| | | msrA_reverse | 23 |
| | Probe 8 | msrA_probe | 24 |

(II) Methods for Determining Antibiotic Resistance of MRSA and Other *Staphylococcus* Strains In order to screen for agents that are effective in limiting MRSA growth, or killing MRSA, in addition to culture-based methods, a rapid, sensitive and high throughput method to confirm that the MRSA is not resistant to certain antibiotic agents is necessary. With a sample known or identified to contain MRSA, a method able to determine the presence of an antibiotic agent resistance gene rapidly and accurately may be used to determine MRSA resistance, and thus, rule out the agent as a treatment regime.

(a) Receiving Samples Known or Determined to Contain MRSA or Other *Staphylococcus* Strains Samples that may be used for MRSA, MRSE or other *Staphylococcus* strains' resistance identification may include, but are not limited to, collected samples from various subjects, which are detailed in Section I (b). These samples are known or determined to contain MRSA using known methods, including but not limited to, the multiplex assay disclosed in U.S. provisional application 61/432,511 hereby incorporated by reference.

(b) Detecting the Absence or Presence of an Antibiotic Resistance Gene in the Sample Methods identifying MRSA, MRSE or other *Staphylococcus* strains' resistance to certain antibiotic agents may include those used to detect the absence or presence of antibiotic resistance genes in nucleic acids, or alleles and biomarkers thereof, include PCR, RT-PCR, hybridization, sequencing, and any combination of the above methods.

A nucleic acid may be added to a sample by any of a number of methods including manual methods, mechanical methods, or any combination thereof. The presence of the allele may be signified by any of a number of methods including amplification of a specific nucleic acid sequence, sequencing of a native or amplified nucleic acid, or the detection of a label either bound to or released from the nucleic acid. Addition of the nucleic acid to the sample also encompasses addition of the nucleic acid to a sample in which the target allele to which the nucleic acid has specificity is absent.

(i) PCR

Nucleic acids that may be selectively and specifically amplified from a template nucleic acid contained in a sample. In some nucleic amplification methods, the copies are generated exponentially. Non-limiting nucleic acid amplification methods known in the art include: the polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with Klenow or any other RNA polymerase, or any other method by which copies of a desired sequence are generated.

Polymerase Chain Reaction (PCR) is a highly efficient method of amplifying template DNA, generally involving the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example, 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probe is complimentary to a sequence within the target sequence downstream from either the upstream or downstream primer. Probes may include one or more labels. A label may be any substance capable of aiding a machine, detector, sensor, device, or enhanced or unenhanced human eye, in differentiating a labeled composition from an unlabeled composition. Examples of labels include, but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^{3}H$, $^{14}C$, $^{32}P$, $^{35}S$, or any other compound capable of emitting radiation, rhodamine, 4-(4'-dimethyl-amino-phenylazo)benzoic acid ("Dabcyl"); 4-(4'-dimethyl-amino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof, or any other compound that may be differentially detected. The label may also include one or more fluorescent dyes optimized for use in genotyping. Examples of such dyes include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ-.PCR facilitating the reading of the target amplification.

Either primers along or primers with probes, as described above, will allow a quantification of the amount of specific template DNA present in the initial sample. In addition, RNA may be detected by PCR analysis by first creating a DNA template from RNA through a reverse transcriptase enzyme. In some aspects of the invention, the allele may be detected by quantitative PCR analysis facilitating genotyping analysis of the samples.

As an exemplary example, the use of dual-labeled oligonucleotide probes in PCR reactions is disclosed in U.S. Pat.

No. 5,716,784 to DiCesare. In the PCR step of the multiplex RT-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Apparatus suitable for detection include but not limited to Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex RT-PCR/PCR can also be performed in other real-time PCR systems with multiplexing capabilities.

In multiplex PCR assays, relative quantification is often used to determine the changes in steady-state mRNA levels of a gene across multiple samples and describe the level of mRNA in reference to the levels of an internal control RNA (reference). The control RNA may be co-amplified in the same tube in a multiplex assay or may be amplified in a separate tube. Generally, the control RNA may be a house keeping gene, or gene with constitutive expression, or a standard with known concentration. In relative quantification, however, it does not require standards with known concentrations and the reference can be any transcript, as long as its sequence is known. Relative quantification is based on the expression levels of a target gene versus one or more reference gene(s) and in many experiments it is adequate for investigating physiological changes in gene expression levels. To calculate the expression of a target gene in relation to an adequate reference gene various mathematical models are established. Calculations are based on the comparison of the distinct cycle determined by various methods, e.g. crossing points (CP) and cycle threshold values (Ct) at a constant level of fluorescence; or CP acquisition according to established mathematic algorithm.

The algorithm for Ct values in RT-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should not be amplification in the RT-PCR reaction.

Alternatively, the Cp value may be utilized. Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

(ii) Hybridization

In addition to PCR, which is capable of detecting the presence of antibiotic resistance genes, genotyping analysis may also be performed using a probe that is capable of hybridizing to a nucleic acid sequence of interest. Hybridization sometimes is applicable for quantification (microarray, for example), and it is capable of detecting the presence of a target recognizable to the probe. Probes may include nucleic acids, oligonucleotides (DNA, or RNA), proteins, protein complexes, conjugates, natural ligands, small molecules, nanoparticles, or any combination of molecules that includes one or more of the above, or any other molecular entity capable of specific binding to any allele, whether such molecular entity exists now or is yet to be disclosed. In one aspect of the invention, the probe comprises an oligonucleotide. The description of oligonucleotide is in Section I (ii).

Methods of detecting a gene or an allele generally involve assessing their expression level through their transcriptional or translational products such as a RNA or protein molecule. The expression of a gene or an allele may be assessed by any of a number of methods used currently in the art and yet to be developed. Examples include any nucleic acid detection method, including the following nonlimiting examples, microarray analysis, RNA in situ hybridization, RNAse protection assay, Northern blot. Other examples include any process of detecting expression that uses an antibody, including the following nonlimiting examples, flow cytometry, immunohistochemistry, ELISA, Western blot, Northwestern blot, and immunoaffinity chromatography. Antibodies may be monoclonal, polyclonal, or any antibody fragment including, for example, Fab, $F(ab)_2$, Fv, scFv, phage display antibody, peptibody, multispecific ligand, or any other reagent with specific binding to a target. Other methods of assessing protein expression include the following nonlimiting examples: HPLC, mass spectrometry, protein microarray analysis, PAGE analysis, isoelectric focusing, 2-D gel electrophoresis, and enzymatic assays.

In some aspects of the invention, the presence of an allele may be established by binding to probes on a microarray such as a DNA chip. Examples of DNA chips include chips in which a number of single stranded oligonucleotide probes are affixed to a solid substrate such as silicon glass. Oligonucleotides with a sequence complementary to an allele are capable of specifically binding to that allele to the exclusion of alleles that differ from the specific allele by one or more nucleotides. Labeled sample DNA is hybridized to the oligonucleotides and detection of the label is correlated with binding of the sample, and consequently, the presence of the allele in the sample.

In allele-specific hybridization, oligonucleotide sequences representing all possible variations at a polymorphic site are included on a chip. The chip and sample are subject to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be, labeled with a label of known molecular weight.

A nucleic acid probe may be affixed to a substrate. Alternatively, a sample may be affixed to the substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, either singly or in the presence of one or more additional probes or samples as is exemplified in a microarray. Examples of substrate materials include, but are not limited to, polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A nucleic acid probe may include a label. A label may be any substance capable of aiding a machine, detector, sensor, device, or enhanced or unenhanced human eye, in differentiating a labeled composition from an unlabeled composition. Examples of labels include, but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethyl-amino-phenylazo)benzoic acid ("Dabcyl"); 4-(4'-dimethyl-amino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of such dyes include, but are not limited to: dR110, 5-FAM, 6FAM, dR6G, JOE, HEX, VIC, TET, dTAMRA, TAMRA, NED, dROX, PET, BHQ+, Gold540, and LIZ.

(iii) Sequencing

Methods of detecting the presence of a gene or an allele further include, but are not limited to, any form of DNA sequencing including Sanger, next generation sequencing, pyrosequencing, massively parallel sequencing, pooled, and barcoded DNA sequencing, or any other sequencing method now known or yet to be disclosed; or any other method that allows the detection of a particular nucleic acid sequence within a sample or enables the differentiation of one nucleic acid from another nucleic acid that differs from the first nucleic acid by one or more nucleotides or any combination of these.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP) are added to each of four reactions (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a pyrophosphate upon nucleotide incorporation. An ATP sulfurylase enzyme converts pyrophosphate into ATP which in turn catalyzes the conversion of luciferin to oxyluciferin which results in the generation of visible light that is then detected by a camera.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment. For example, in SOLID sequencing (one of many types of massively parallel sequencing methods/platforms), the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

(e) Preferred Embodiments

A group of exemplary embodiments is shown in Table A. The present invention provides, in one embodiment, that assay 1—vanA assay, applying primer set 1, represented by SEQ ID NO. 1 and 2, and/or probe 1, represented by SEQ ID NO. 3, may be carried out to determine vancomycin resistance of a *Staphylococcus* strain.

In another embodiment, assay 2—aacA assay, applying primer set 2, represented by SEQ ID NO. 4 and 5, and/or probe 2, represented by SEQ ID NO. 6, may be carried out to determine aminoglycoside resistance of a *Staphylococcus* strain.

In one embodiment, assay 3—blaZ assay, applying primer set 3, represented by SEQ ID NO. 7 and 8, and/or probe 3, represented by SEQ ID NO. 9, may be carried out to determine penicillin resistance of a *Staphylococcus* strain.

In one embodiment, assay 4—ermA assay, applying primer set 4, represented by SEQ ID NO. 10 and 11, and/or probe 4, represented by SEQ ID NO. 12, may be carried out to determine macrolide resistance of a *Staphylococcus* strain.

In one embodiment, assay 5—ermC assay, applying primer set 5, represented by SEQ ID NO. 13 and 14, and/or probe 5, represented by SEQ ID NO. 15, may be carried out to determine macrolide resistance of a *Staphylococcus* strain as well.

In one embodiment, assay 6—tetK assay, applying primer set 6, represented by SEQ ID NO. 16 and 17, and/or probe 6, represented by SEQ ID NO. 18, may be carried out to determine tetracycline resistance of a *Staphylococcus* strain.

In one embodiment, assay 7—tetM assay, applying primer set 7, represented by SEQ ID NO. 19 and 20, and/or probe 7, represented by SEQ ID NO. 21, may be carried out to determine tetracycline resistance of a *Staphylococcus* strain as well.

In one embodiment, assay 8—msrA assay, applying primer set 8, represented by SEQ ID NO. 22 and 23, and/or probe 8, represented by SEQ ID NO. 24, may be carried out to determine macrolide resistance of a *Staphylococcus* strain as well.

In one preferred embodiment, a multiplex assay may be carried out by applying more than one set of primers and probes in one RT-PCR reaction to determine the profile of antibiotic resistance or susceptibility to multiple agents of a *Staphylococcus* strain.

The combination of assays in a multiplex RT-PCR/PCR assay is through applying multiple sets of primers and/or probes, respectively, in one RT-PCR reaction. The multiplex RT-PCR/PCR assay may comprise any number or any combination of individual assays, such as 2 assays, 3 assays, 4 assays or beyond, to the extent of the capability of PCR or hybridization platform used.

(III) Kits

Still another aspect of the invention encompasses kits for determining MRSA or other *Staphylococcus* strains' resistance to one or more antibiotic agents through detecting the presence of the resistance gene for respective antibiotic agent. In preferred embodiments, the kits comprise one or more primer sets and probes for assays chosen from vanA assay, aacA assay, blaZ assay, ermA assay, ermC assay, tetK assay, tetM assay and msrA assay. As described in detail in previous sections and in Table A: vanA assay can determine vancomycin resistance of a *Staphylococcus* strain by applying primer set 1, represented by SEQ ID NO. 1 and 2 and/or probe 1, represented by SEQ ID NO. 3; aacA assay can determine aminoglycoside resistance of a *Staphylococcus* strain by applying primer set 2, represented by SEQ ID NO. 4 and 5, and/or probe 2, represented by SEQ ID NO. 6; blaZ can determine penicillin resistance of a *Staphylococcus* strain by applying primer set 3, represented by SEQ ID NO. 7 and 8, and/or probe 3, represented by SEQ ID NO. 9; ermA assay can determine macrolide resistance of a *Staphylococcus* strain by applying primer set 4, represented by SEQ ID NO. 10 and 11, and/or probe 4, represented by SEQ ID NO. 12; ermC assay can determine macrolide resistance of a *Staphylococcus* strain as well by applying primer set 5, represented by SEQ ID NO. 13 and 14, and/or probe 5, represented by SEQ ID NO. 15; tetK assay can determine tetracycline resistance of a *Staphylococcus* strain by applying primer set 6, represented by SEQ ID NO. 16 and 17, and/or probe 6, represented by SEQ ID NO. 18; tetM assay can determine tetracycline resistance of a *Staphylococcus* strain by applying primer set 7, represented by SEQ ID NO. 19 and 20, and/or probe 7, represented by SEQ ID NO. 21; and msrA assay can determine macrolide resistance of a *Staphylococcus* strain by applying primer set 8, represented by SEQ ID NO. 22 and 23, and/or probe 8, represented by SEQ ID NO. 24.

The multiplex assay is a type of analysis chosen from PCR, RT-PCR, sequencing, hybridization, and any combination thereof, in which a primer set or a probe or both is applied to detect the presence of more than one targeted sequences chosen from *S. aureus* vanA, aacA, blaZ, ermA, ermC, tetK, tetM and msrA genes. The assays detecting respective targeted gene may be carried out individually in multiple separate reaction systems or in one combined and mixed reaction system for PCR, RT-PCR, sequencing, hybridization, or any combination thereof. In one preferred embodiment, the kit comprises primer sets and probes for a multiplex assay comprising at least two assays chosen from vanA, aacA, blaZ, ermA, ermC, tetK, tetM and msrA assays.

The kit that facilitates nucleic acid based assays to determine MRSA or other *Staphylococcus* strains' resistance to one or more antibiotic agents through detecting the presence of the resistance gene for respective antibiotic agent may further comprise one or more of the following: nucleic acid extraction reagents, controls, disposable cartridges, labeling reagents, enzymes including PCR amplification reagents such as the DNA polymerases Taq or Pfu, reverse transcriptase, or one or more other polymerases, and/or reagents that facilitate hybridization.

In another embodiment, the kit may further comprise a label that can be used to label the primer or probe oligonucleotide. A label may be any substance capable of aiding a machine, detector, sensor, device, or enhanced or unenhanced human eye, in differentiating a sample that that displays positive expression from a sample that displays reduced expression. Examples of labels include but are not limited to: a radioactive isotope or chelate thereof, a dye (fluorescent or nonfluorescent,) stain, enzyme, or nonradioactive metal. Specific examples include but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethylaminophenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylene diamine tetra-acetic acid ("EDTA") and derivatives thereof or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, BHQ+, Gold540, and LIZ.

In yet anther embodiment, the primers and probes in the kit may have been labeled, and can be applied without labeling process in PCR, sequencing reaction, or binding to a solid substrate such as oligonucleotide array.

A kit for determining MRSA or other *Staphylococcus* strain resistance to one or more antibiotic agents through detecting the presence of the resistance gene for a respective antibiotic agent may also comprise instructions for use. In one embodiment, the kit may further comprise an indication that links the output of the assays provided by the kit to a particular result. For example, an indication may provide guidance to associate the presence of one or more sequences to the identification of a particular antibiotic resistance. The indication may contain a standard curve configured to indicate the presence of one or more resistance genes in a sample. The output of the assay may be in a form of a particular sequence, a particular genotype, a particular ΔCt level in a real-time quantitative PCR reaction, a level of fluorescence or radioactive decay, a value derived from a standard curve, or from a positive or negative control, or any combination of these and other outputs. The indication may be printed on a writing that may be included in the kit or it may be posted on the Internet or embedded in a software package. The writing may include graphical depictions of results such as a photomicrograph or amplification plot.

A kit for determining MRSA or other *Staphylococcus* strain resistance to one or more antibiotic agents through detecting the presence of the resistance gene for a respective antibiotic agent may further comprise a device used to collect the sample. Such devices may include, but need not be limited to: swabs, needles, blood collection tubes, wipes, or any other apparatus that may be used to collect a biological sample from a patient or from the environment now known or yet to be disclosed.

EXAMPLES

The following examples illustrate certain aspects of the invention.

Example 1

Specificity and Selectivity

The present invention discloses real time PCR assays designed to determine MRSA and other *Staphylococcus* strain resistance to one or more antibiotic agents through detecting the presence of the resistance gene for a respective antibiotic agent. The performance of the individual assays using panels of bacterial isolates is shown in Tables 2-7. Tested strains were clinically isolated *Staphylococcus*. These assays may be also used in combination to profile MRSA or other *Staphylococcus* strain resistance to a number of antibiotic agents by using the vanA gene as a marker, whose presence indicates vancomycin resistance; using the aacA gene as a marker, whose presence indicates aminoglycoside resistance; using the blaZ gene as a marker, the presence of which indicates a high likelihood of penicillin resistance; using ermA and ermC genes as markers, and the presence of ermA indicates macrolide resistance; and using the msrA gene as a marker, the presence of which indicates macrolide resistance. When using tetK and tetM genes as markers, several susceptible strains are positive for tetM. These results suggest that the assay could be detecting a tetM gene that is not being expressed or the susceptibility status from the clinic is inaccurate.

TABLE 1

Primer and probe sets

| Target | Description | Sequence | SEQ ID NO. |
|---|---|---|---|
| vanA | vanA_forward | CGGCTCGACTTCCTGATGA | 1 |
|  | vanA_reverse | TGTGCGGTATTGGGAAACAG | 2 |
|  | VanA_Probe | ACGAAAGATTCCGTACTGCAGCC | 3 |
| aacA | aacA_forward | GCCACACTATCATAACCACTACCGA | 4 |
|  | aacA_reverse | TCCAAGAGCAATAAGGGCATACCAA | 5 |
|  | aacA_probe | CATTGCCTTAACATTTGTGGC | 6 |
| blaZ | blaZ_forward | ACACTCTTGGCGGTTTCACT | 7 |
|  | blaZ_reverse | CCTAAGGGCCAATCTGAACCTATT | 8 |
|  | blaZ_probe | CAACTTATCATTTGGCTTATCAC | 9 |
| ermA | ermA_forward | CAACCATTGATTTCAAAGAAGGACTAC | 10 |
|  | ermA_reverse | TCAAAGCCTGTCGGAATTGGT | 11 |
|  | ermA_probe | AGTGGGTAAACCGTGAATATCGTG | 12 |
| ermC | ermC_forward | ATTTAATCGTGGAATACGAGTTTGCTAA | 13 |
|  | ermC_reverse | CGTCAATTCCTGCATGTTTTAAGG | 14 |
|  | ermC_probe | CCTAAACCTAAAGTGAATAGCTCAC | 15 |

TABLE 1-continued

Primer and probe sets

| Target | Description | Sequence | SEQ ID NO. |
|---|---|---|---|
| tetK | tetK_forward | AGTTTGAGCTGTCTTGGTTCATTG | 16 |
|  | tetK_reverse | TGCAGCAGATCCTACTCCTTGTAC | 17 |
|  | tetK_Probe | TTGCTTTTATTGGTCACAATCAC | 18 |
| tetM | tetM_forward | CTTTCTGGGCTTCCATTGGTTTATC | 19 |
|  | tetM_reverse | CGAGCTCTCATACTGCATTCCA | 20 |
|  | tetM_probe | TTCCCAACGGAAGCGGTGATACA | 21 |
| msrA | msrA_forward | CTTCTTCCAAATGTTCCATTCTTTTT | 22 |
|  | msrA_reverse | ACCAGATCGTTTAAGTGCATCAAA | 23 |
|  | msrA_probe | TGAGCAGCCTTCTCAACCGTGCCT | 24 |

TABLE 2

Detection of the vancomycin resistance gene using vanA assay (SEQ ID NO. 1, SEQ ID NO. 2, SEQ ID NO. 3).

| Results: | Resistant | Susceptible | Unknown |
|---|---|---|---|
| Detected | 6 | 0 | 0 |
| Did not detect | 0 | 81 | 0 |
| Total screened | 6 | 81 | 0 |

TABLE 3

Detection of the aminoglycoside resistance gene using the aacA assay (SEQ ID NO. 4, SEQ ID NO. 5, and SEQ ID NO. 6)

| Results: | Resistant | Susceptible | Unknown |
|---|---|---|---|
| Detected | 6 | 0 | 0 |
| Did not detect | 1 | 66 | 18 |
| Total screened | 7 | 66 | 18 |

TABLE 4

Detection of penicillin resistance gene using blaZ assay (SEQ ID NO. 7, SEQ ID NO. 8, and SEQ ID NO. 9).

| Results: | Resistant | Susceptible | Intermediate | Unknown |
|---|---|---|---|---|
| Detected | 70 | 2 | 1* late | 12 |
| Did not detect | 23 | 6 | 3 | 60 |
| Total screened | 93 | 8 | 4 | 72 |

TABLE 5

Detection of macrolide resistance genes using the ermA
(SEQ ID NO 10, SEQ ID NO. 11, SEQ ID NO. 12) and ermC
(SEQ ID NO. 13, SEQ ID NO. 14, and SEQ ID NO. 15) multiplex.

| Results: | Resistant | Susceptible | Intermediate | Unknown |
|---|---|---|---|---|
| ermA assay detected | 38 | 2 | 1 | 1 |
| ermC assay detected | 0 | 0 | 0 | 0 |
| Both detected | 0 | 0 | 0 | 0 |
| Neither detected | 24 | 10 | 5 | 8 |
| Total screened | 62 | 12 | 6 | 9 |

TABLE 6

Detection of tetracycline resistance genes using tetK
(SEQ ID NO. 16, SEQ ID NO. 17, and SEQ ID NO. 18), and tetM
(SEQ ID NO. 19, SEQ ID NO. 20, and SEQ ID NO. 21) multiplex.

| Results: | Resistant | Susceptible | Unknown |
|---|---|---|---|
| tetM assay detected | 4 | 10 | 14 |
| tetK assay detected | 0 | 0 | 0 |
| Both detected | 0 | 0 | 0 |
| Neither detected | 11 | 64 | 75 |
| Total screened | 15 | 74 | 89 |

TABLE 7

Detection of macrolide resistance genes using the msrA
(SEQ ID NO 22, SEQ ID NO. 23, SEQ ID NO. 24) multiplex.

| Results: | Resistant | Susceptible | Unknown |
|---|---|---|---|
| msrA assay detected | 2 | 0 | 7 |
| msrA did not detected | 4 | 14 | 24 |
| Total screened | 6 | 14 | 31 |

The assays may be used singly, in any combination with each other, or with additional assays to ascertain whether or not an antibiotic resistance gene is present in a sample. This includes performance of all assays separately, in a single PCR run, in a single sequencing reaction, on a single array, or in any other combination now known or yet to be disclosed.

Example 2

Additional Sequences that Can be Used to Develop Similar Assays to Determine MRSA Susceptibility Additional sequences that can be used to develop similar assays as disclosed herein to determine MRSA susceptibility further include the following: SEQ ID NO. 25—*S. aureus* vanA, SEQ ID NO. 26—*S. aureus* aacA, SEQ ID NO. 27—*S. epidermidis* blaZ, SEQ ID NO. 28—*S. aureus* ermA, SEQ ID NO. 29 *S. aureus* ermC, SEQ ID NO. 30—*S. aureus* tetK, SEQ ID NO. 31—*S. aureus* tetM, which are detailed in the Sequence Listings.

The foregoing description of a preferred embodiment and best mode of the invention known to the applicant at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

What is claimed is:

1. A profiling assay for determining a *Staphylococcus* strain's resistance to one or more antibiotic agents, the profiling assay comprising a sequence-specific vanA assay, a sequence-specific aacA assay, and one or more sequence-specific assays chosen from a group consisting of a sequence-specific, blaZ assay, a sequence-specific ermA assay, a sequence-specific ermC assay, a sequence-specific tetK assay, a sequence-specific tetM assay, and a sequence-specific msrA assay, wherein the profiling assay is configured to screen the *Staphylococcus* strain using the sequence-specific assays to amplify selected target genes and to analyze results of the sequence-specific assays using relative quantification of expression of the genes targeted by the sequence-specific assays, wherein the sequence-specific vanA assay is used to determine the *Staphylococcus* strain's resistance to aminoglycoside and comprises an oligonucleotide sequence consisting of SEQ ID NO: 1 and an oligonucleotide sequence consisting of SEQ ID NO: 2, and a probe comprising a label and a sequence consisting of SEQ ID NO: 3;

wherein the sequence-specific aacA assay is used to determine the *Staphylococcus* strain's resistance to vancomycin and comprises an oligonucleotide sequence consisting of SEQ ID NO: 4 and an oligonucleotide sequence consisting of SEQ ID NO: 5, and a probe comprising a label and a sequence consisting of SEQ ID NO: 6;

wherein the sequence-specific blaZ assay is used to determine the *Staphylococcus* strain's resistance to penicillin and comprises an oligonucleotide sequence consisting of SEQ ID NO: 7 and an oligonucleotide sequence consisting of SEQ ID NO: 8 and a probe comprising a label and a sequence consisting of SEQ ID NO: 9;

wherein the sequence-specific ermA assay is used to determine the *Staphylococcus* strain's resistance to macrolide and comprises an oligonucleotide sequence consisting of SEQ ID NO: 10 and an oligonucleotide sequence consisting of SEQ ID NO: 11 and a probe comprising a label and a sequence consisting of SEQ ID NO: 12;

wherein the sequence-specific ermC assay is used to determine the *Staphylococcus* strain's resistance to macrolide and comprises an oligonucleotide sequence consisting of SEQ ID NO: 13 and an oligonucleotide sequence consisting of SEQ ID NO: 14 and a probe comprising a label and a sequence consisting of SEQ ID NO: 15;

wherein the sequence-specific tetK assay is used to determine the *Staphylococcus* strain's susceptibility to tetracycline and comprises an oligonucleotide sequence consisting of SEQ ID NO: 16 and an oligonucleotide sequence consisting of SEQ ID NO:17 and a probe comprising a label and a sequence consisting SEQ ID NO: 18;

wherein the sequence-specific tetM assay is used to determine the *Staphylococcus* strain's susceptibility to tetracycline and comprises an oligonucleotide sequence consisting of the sequence set forth in SEQ ID NO: 19 and an oligonucleotide sequence consisting of SEQ ID NO: 20 and a probe comprising a label and a sequence consisting of SEQ ID NO: 21; and wherein the sequence-specific msrA assay is used to determine the *Staphylococcus* strain's resistance to macrolide and comprises an oligonucleotide sequence consisting of SEQ ID NO: 22 and an oligonucleotide sequence consisting of SEQ ID NO: 23 and a probe comprising a label and a sequence consisting of SEQ ID NO: 24.

2. The profiling assay of claim 1, wherein the *Staphylococcus* strain is selected from the group consisting of MRSA, MSSA, MRSE, and MSSE.

3. The profiling assay of claim 1, the assay is a type of analysis chosen from PCR and RT-PCR.

4. The profiling assay of claim 1, wherein the assays comprise the sequence-specific vanA assay, the sequence-specific aacA assay, the sequence-specific ermA assay, and the sequence-specific ermC assay.

5. The profiling assay of claim 4, wherein sequence-specific ermA assay and the sequence-specific ermC assay are performed together as a multiplex assay.

6. The profiling assay of claim 1, wherein assays comprise the sequence-specific vanA assay, the sequence-specific aacA assay, the sequence-specific blaZ assay, the sequence-specific ermA assay, the sequence-specific ermC assay, the sequence-specific tetK assay, the sequence-specific tetM assay, and the sequence-specific msrA assay.

7. A method for determining a *Staphylococcus* strain's resistance to one or more antibiotic agents, comprising:

a. receiving a sample comprising *Staphylococcus*;
b. screening the sample by conducting sequence-specific PCR-based assays comprising vanA assay, aacA assay, and one or more sequence-specific assays selected from the group consisting of blaZ assay, ermA assay, ermC assay, tetK assay, tetM assay, and msrA assay, wherein:
the vanA assay comprises a primer set comprising:
  a primer having a sequence consisting of SEQ ID No: 1;
  a primer having a sequence consisting of SEQ ID NO: 2; and
  a probe comprising a label and a sequence consisting of the sequence set forth in SEQ ID NO:3;
the aacA assay comprises a primer set comprising:
  a primer having a sequence consisting of SEQ ID No: 4;
a primer having a sequence consisting of SEQ ID NO: 5; and
  a probe comprising a label and a sequence consisting of SEQ ID NO:6;
the blaZ assay comprises a primer set comprising:
  a primer having a sequence consisting of SEQ ID No: 7;
  a primer having a sequence consisting of SEQ ID NO: 8; and
  a probe comprising a label and a sequence consisting of SEQ ID NO:9;
the ermA assay comprises a primer set comprising:
  a primer having a sequence consisting of SEQ ID No: 10;
  a primer having a sequence consisting of SEQ ID NO: 11; and
  a probe comprising a label and a sequence consisting of SEQ ID NO:12;
the ermC assay comprises a primer set comprising:
  a primer having a sequence consisting of SEQ ID No: 13;
  a primer having a sequence consisting of SEQ ID NO: 14; and
  a probe comprising a label and a sequence consisting of SEQ ID NO:15;
the tetK assay comprises a primer set comprising:
  a primer having a sequence consisting of SEQ ID No: 16;
  a primer having a sequence consisting of SEQ ID NO: 17; and
  a probe comprising a label and a sequence consisting of the sequence set forth in SEQ ID NO:18;
the tetM assay comprises a primer set comprising:
  a primer having a sequence consisting of the sequence set forth in SEQ ID No: 19;
  a primer having a sequence consisting of SEQ ID NO: 20; and
  a probe comprising a label and a sequence consisting of SEQ ID NO:21;
the msrA assay comprises a primer set comprising:
  a primer having a sequence consisting of SEQ ID No: 22;
  a primer having a sequence consisting of SEQ ID NO: 23; and
  a probe comprising a label and a sequence consisting of SEQ ID NO:24;
c. analyzing results obtained from the sequence-specific PCR-based assays to determine the presence or absence of a vanA gene, an aacA gene, and one or more genes selected from the group consisting of: a blaZ gene, an ermA gene, an ermC gene, a tetK gene, a tetM gene and a msrA gene, wherein analyzing the results comprises relative quantification of expression of the genes targeted by the sequence-specific PCR-based assays; and d. identifying the *Staphylococcus* strain contained in the sample as resistant to one or more antibiotics based on the analysis of the selected sequence-specific PCR-based assays.

8. The method of claim 7, wherein the presence of the vanA gene indicates vancomycin resistance;

wherein the presence of the aacA gene indicates aminoglycoside resistance;

wherein the presence of the blaZ gene indicates penicillin resistance;

wherein the presence of ermA and ermC indicate macrolide resistance;

wherein the absence of tetM and tetK indicate susceptibility to tetracycline; and wherein the presence of msrA indicates macrolide resistance.

9. The method of claim 7, wherein the sample comprises MRSA, MRSE, MSSA, or MSSE.

10. The method of claim 7, wherein one or more of the probes comprise a label.

11. The method of claim 7, wherein the ermA assay and the ermC assay are performed as a single multiplex assay.

12. The method of claim 7, wherein the sequence-specific PCR-based assays comprising the vanA assay, the aacA assay, the ermA assay, and the ermC assay.

13. The method of claim 12, wherein the ermA assay and the ermC assay are performed as a single multiplex assay.

14. The method of claim 7, wherein the sequence-specific PCR-based assays comprising the vanA assay, the aacA assay, the ermA assay, the ermC assay, the blaZ assay, the tetM assay, the tetK assay, and the msrA assay.

15. The method of claim 14, wherein the erm A and ermC assays and the tetM and tetK assays are performed as single multiplex assays, respectively.

* * * * *

SEQUENCE LISTING

<160> NUMBER OF SEQ ID NOS: 31

<210> SEQ ID NO 1
<211> LENGTH: 19
<212> TYPE: DNA
<213> ORGANISM: Artificial Sequence
<220> FEATURE:
<223> OTHER INFORMATION: vanA forward

<400> SEQUENCE: 1
cggctcgact tcctgatga                                                19

<210> SEQ ID NO 2
<211> LENGTH: 20
<212> TYPE: DNA
<213> ORGANISM: Artificial Sequence
<220> FEATURE:
<223> OTHER INFORMATION: vanA reverse

<400> SEQUENCE: 2
tgtgcggtat tgggaaacag                                               20

```
<210> SEQ ID NO 3
<211> LENGTH: 23
<212> TYPE: DNA
<213> ORGANISM: Artificial Sequence
<220> FEATURE:
<223> OTHER INFORMATION: vanA probe

<400> SEQUENCE: 3
acgaaagatt ccgtactgca gcc                                          23

<210> SEQ ID NO 4
<211> LENGTH: 25
<212> TYPE: DNA
<213> ORGANISM: Artificial Sequence
<220> FEATURE:
<223> OTHER INFORMATION: aacA forward

<400> SEQUENCE: 4
gccacactat cataaccact accga                                        25

<210> SEQ ID NO 5
<211> LENGTH: 25
<212> TYPE: DNA
<213> ORGANISM: Artificial Sequence
<220> FEATURE:
<223> OTHER INFORMATION: aacA reverse

<400> SEQUENCE: 5
tccaagagca ataagggcat accaa                                        25

<210> SEQ ID NO 6
<211> LENGTH: 21
<212> TYPE: DNA
<213> ORGANISM: Artificial Sequence
<220> FEATURE:
<223> OTHER INFORMATION: aacA probe

<400> SEQUENCE: 6
cattgcctta acatttgtgg c                                            21

<210> SEQ ID NO 7
<211> LENGTH: 20
<212> TYPE: DNA
<213> ORGANISM: Artificial Sequence
<220> FEATURE:
<223> OTHER INFORMATION: blaZ forward

<400> SEQUENCE: 7
acactcttgg cggtttcact                                              20

<210> SEQ ID NO 8
<211> LENGTH: 24
<212> TYPE: DNA
<213> ORGANISM: Artificial Sequence
<220> FEATURE:
<223> OTHER INFORMATION: blaZ reverse

<400> SEQUENCE: 8
cctaagggcc aatctgaacc tatt                                         24

<210> SEQ ID NO 9
<211> LENGTH: 23
<212> TYPE: DNA
<213> ORGANISM: Artificial Sequence
<220> FEATURE:
<223> OTHER INFORMATION: blaZ probe
```

```
<400> SEQUENCE: 9
caacttatca tttggcttat cac                                    23

<210> SEQ ID NO 10
<211> LENGTH: 27
<212> TYPE: DNA
<213> ORGANISM: Artificial Sequence
<220> FEATURE:
<223> OTHER INFORMATION: ermA forward

<400> SEQUENCE: 10
caaccattga tttcaaagaa ggactac                                27

<210> SEQ ID NO 11
<211> LENGTH: 21
<212> TYPE: DNA
<213> ORGANISM: Artificial Sequence
<220> FEATURE:
<223> OTHER INFORMATION: ermA reverse

<400> SEQUENCE: 11
tcaaagcctg tcggaattgg t                                      21

<210> SEQ ID NO 12
<211> LENGTH: 24
<212> TYPE: DNA
<213> ORGANISM: Artificial Sequence
<220> FEATURE:
<223> OTHER INFORMATION: ermA probe

<400> SEQUENCE: 12
agtgggtaaa ccgtgaatat cgtg                                   24

<210> SEQ ID NO 13
<211> LENGTH: 28
<212> TYPE: DNA
<213> ORGANISM: Artificial Sequence
<220> FEATURE:
<223> OTHER INFORMATION: ermC forward

<400> SEQUENCE: 13
atttaatcgt ggaatacgag tttgctaa                               28

<210> SEQ ID NO 14
<211> LENGTH: 24
<212> TYPE: DNA
<213> ORGANISM: Artificial Sequence
<220> FEATURE:
<223> OTHER INFORMATION: ermC reverse

<400> SEQUENCE: 14
cgtcaattcc tgcatgtttt aagg                                   24

<210> SEQ ID NO 15
<211> LENGTH: 24
<212> TYPE: DNA
<213> ORGANISM: Artificial Sequence
<220> FEATURE:
<223> OTHER INFORMATION: ermC probe

<400> SEQUENCE: 15
cctaaaccta aagtgaatag ctca                                   24

<210> SEQ ID NO 16
<211> LENGTH: 24
```

```
<212> TYPE: DNA
<213> ORGANISM: Artificial Sequence
<220> FEATURE:
<223> OTHER INFORMATION: tetK forward

<400> SEQUENCE: 16
agtttgagct gtcttggttc attg                                          24

<210> SEQ ID NO 17
<211> LENGTH: 24
<212> TYPE: DNA
<213> ORGANISM: Artificial Sequence
<220> FEATURE:
<223> OTHER INFORMATION: tetK reverse

<400> SEQUENCE: 17
tgcagcagat cctactcctt gtac                                          24

<210> SEQ ID NO 18
<211> LENGTH: 22
<212> TYPE: DNA
<213> ORGANISM: Artificial Sequence
<220> FEATURE:
<223> OTHER INFORMATION: tetK probe

<400> SEQUENCE: 18
ttgcttttat tggtcacaat ca                                            22

<210> SEQ ID NO 19
<211> LENGTH: 25
<212> TYPE: DNA
<213> ORGANISM: Artificial Sequence
<220> FEATURE:
<223> OTHER INFORMATION: tetM forward

<400> SEQUENCE: 19
ctttctgggc ttccattggt ttatc                                         25

<210> SEQ ID NO 20
<211> LENGTH: 22
<212> TYPE: DNA
<213> ORGANISM: Artificial Sequence
<220> FEATURE:
<223> OTHER INFORMATION: tetM reverse

<400> SEQUENCE: 20
cgagctctca tactgcattc ca                                            22

<210> SEQ ID NO 21
<211> LENGTH: 23
<212> TYPE: DNA
<213> ORGANISM: Artificial Sequence
<220> FEATURE:
<223> OTHER INFORMATION: tetM probe

<400> SEQUENCE: 21
ttcccaacgg aagcggtgat aca                                           23

<210> SEQ ID NO 22
<211> LENGTH: 26
<212> TYPE: DNA
<213> ORGANISM: Artificial Sequence
<220> FEATURE:
<223> OTHER INFORMATION: msrA forward

<400> SEQUENCE: 22
```
cttcttccaa atgttccatt cttttt                                              26

<210> SEQ ID NO 23
<211> LENGTH: 24
<212> TYPE: DNA
<213> ORGANISM: Artificial Sequence
<220> FEATURE:
<223> OTHER INFORMATION: msrA reverse

<400> SEQUENCE: 23
accagatcgt ttaagtgcat caaa                                                24

<210> SEQ ID NO 24
<211> LENGTH: 24
<212> TYPE: DNA
<213> ORGANISM: Artificial Sequence
<220> FEATURE:
<223> OTHER INFORMATION: msrA probe

<400> SEQUENCE: 24
tgagcagcct tctcaaccgt gcct                                                24

<210> SEQ ID NO 25
<211> LENGTH: 1032
<212> TYPE: DNA
<213> ORGANISM: Staphylococcus aureus
<220> FEATURE:
<221> NAME/KEY: misc_feature
<223> OTHER INFORMATION: vanA

<400> SEQUENCE: 25
atgaatagaa taaaagttgc aatactgttt gggggttgct cagaggagca tgacgtatcg         60
gtaaaatctg caatagagat agccgctaac attaataaag aaaaatacga gccgttatac       120
attggaatta cgaaatctgg tgtatggaaa atgtgcgaaa aaccttgcgc ggaatgggaa       180
aacgacaatt gctattcagc tgtactctcg ccggataaaa aatgcacgg attacttgtt        240 aaaaagaacc atgaatatga aatcaaccat gttgatgtag cattttcagc tttgcatggc       300
aagtcaggtg aagatggatc catacaaggt ctgtttgaat tgtccggtat cccttttgta       360
ggctgcgata ttcaaagctc agcaatttgt atggacaaat cgttgacata catcgttgcg       420
aaaaatgctg gatagctac tcccgccttt tgggttatta ataaagatga taggccggtg        480
gcagctacgt ttacctatcc tgttttttgtt aagccggcgc gttcaggctc atccttcggt      540
gtgaaaaaag tcaatagcgc ggacgaattg gactacgcaa ttgaatcggc aagacaatat       600
gacagcaaaa tcttaattga gcaggctgtt tcgggctgtg aggtcggttg tgcggtattg       660
ggaaacagtg ccgcgttagt tgttggcgag gtggaccaaa tcaggctgca gtacggaatc       720
tttcgtattc atcaggaagt cgagccggaa aaaggctctg aaaacgcagt tataaccgtt       780
cccgcagacc tttcagcaga ggagcgagga cggatacagg aaacggcaaa aaaatatat       840 aaagcgctcg gctgtagagg tctagcccgt gtggatatgt ttttacaaga taacggccgc       900
attgtactga acgaagtcaa tactctgccc ggtttcacgt catacagtcg ttatccccgt       960
atgatggccg ctgcaggtat tgcacttccc gaactgattg accgcttgat cgtattagcg      1020
ttaaaggggt ga                                                           1032

<210> SEQ ID NO 26
<211> LENGTH: 1440
<212> TYPE: DNA
<213> ORGANISM: Staphylococcus aureus
<220> FEATURE:

<221> NAME/KEY: misc_feature
<223> OTHER INFORMATION: aacA

<400> SEQUENCE: 26

```
tcaatcttta taagtccttt tataaatttc ttttctacca ttttcgataa attcctgttt     60
aatattttta attccataaa caatagtttc aataggataa tattcttcaa ctatatcttg    120
atattctttt gctttctcaa tatctatatt tccatacatt cttaatatat cttctccaaa    180
atttgttcct atttcttctt cactatcttc aagtaagtat ataaaatcac aatattcatc    240
tataattcca gaatctccaa aatcaattat tccagttaat ctattattgc catctaacaa    300
tagatgatta caactaaaat cattatggca taaacacttt ttaccctcaa aaactgttgt    360
tgcatttagt ctttccataa aactttctat ataatctttt tctatatcag ttaaatcatt    420
ataaatagtt tcacgcaaca atatatactc ttctaataca ttttgtttat tatcaatagt    480
acattcacta atatctgtat aatctaaacc gtgcatttgt cttaaaaaac tggcaatatc    540
tcgtttaac aaattttgtt cttcttctga catagtagaa taaatttctg gtgttaaaaa     600
agttccttta atttctttat aacctagtat agataattca tcactaatat acgaatattc    660
aatattagga atttttacat tagtttctaa atttgtattt aaaaaattat atattgcttt    720
ttcttttgca taaccttttt tcttattagt actaaatttt gttttaaaaa tgtattcatt    780
attaactaaa tatgccacac tatcataacc actaccgatt atttcaatac tatctacttt    840
gaaattatca agtaatgct caattaaata tttcattgcc ttaacatttg tggcattatc     900
atcatatcta tattccatta ataacaatc ttctttttg ccctcgtgta attcatgttc      960
tggcaaatct tcaataattc taaaaccaga tttttggtat gcccttattg ctcttggatt   1020
attttttatga gggtctaaaa taactgcatt agcatttctt tctttttttca aaaattcaaa  1080
aatcaattta atatatcttg taccaattcc tttactccaa taatttggct ctcctataaa   1140
ttgatccata ccatagacta tctcatcagt ttttggataa tgataatcag tatataactc   1200
atcatacatt ttatatattt gtccatatcc aataggaaca ttgttatatt caataattac   1260
tctaaaaact tcatcttccc aaggctctgt ataatgtttt tttaatgatt ctaatgtata   1320
ttttttatct ctaccaccat aaaattctaa tactctttca tcagttaacc attttaacat   1380
caaaggaaaa tcatcatcta ttaaagttct tatacatatt tcattttcaa ctatattcat   1440
```

<210> SEQ ID NO 27
<211> LENGTH: 846
<212> TYPE: DNA
<213> ORGANISM: Staphylococcus aureus
<220> FEATURE:
<221> NAME/KEY: misc_feature
<223> OTHER INFORMATION: blaZ

<400> SEQUENCE: 27

```
ttgaaaagt taatattttt aattgcaatt gctttagttt taagtgcatg taattcaaac      60
agttcacatg ccaaagagtt aaatgattta gaaaaaaaat ataatgctca tattggtgtt    120
tatgctttag atactaaaag tggtaaggaa gtaaaattta attcagataa gagatttgcc    180
tatgcttcga cttcaaaagc gataaatagt gctattttgt tagaacaagt accttataat    240
aagttaaata aaaaaataca tattaacaaa gatgatatag ttgcttattc tcctatttta    300
gaaaatatg taggaaaaga tatcactttta aagaacttta ttgaggcttc aatggcatat    360
agtgataata cagcaaacaa taaaattata aagaaattg tggaatcaa aaagtaaa       420
caacgtctaa aagaactagg agataaagta acaaatccag ttagatatga gatagaatta    480
```

```
aattactatt caccaaagag caaaaaagat acttcaacac ctgctgcttt cggtaagact      540
ttaaataaac ttatcgcaaa tggaaaatta agcaaagaaa acaaaaaatt cttacttgat      600
ttaatgttaa ataataaaag cggagatact ttaattaaag acggtgtttc aaaagactgt      660
aaggttgctg ataaaagtgg tcaagcaata acatatgctt ctagaaatga tgttgctttt      720
gtttatccta agggccaatc tgaacctatt gttttagtca ttttttacgaa taaagacaat     780 aaaagtgata agccaaatga taagttgata agtgaaaccg ccaagagtgt aatgaaggaa     840
ttttaa                                                                846

<210> SEQ ID NO 28
<211> LENGTH: 732
<212> TYPE: DNA
<213> ORGANISM: Staphylococcus aureus
<220> FEATURE:
<221> NAME/KEY: misc_feature
<223> OTHER INFORMATION: ermA

<400> SEQUENCE: 28
atgaaccaga aaaccctaa agacacgcaa aatttttatta cttctaaaaa gcatgtaaaa       60
gaaatattga atcacacgaa tatcagtaaa caagacaacg taatagaaat cggatcagga     120
aaaggacatt ttaccaaaga gctagtcaaa atgagtcgat cagttactgc tatagaaatt     180
gatggaggct tatgtcaagt gactaaagaa gcggtaaacc cctctgagaa tataaaagtg     240
attcaaacgg atattctaaa attttccttc ccaaaacata taaactataa gatatatggt     300
aatattcctt ataacatcag tacgatatt gtcaaaagaa ttacctttga aagtcaggct     360
aaatatagct atcttatcgt tgagaaggga tttgcgaaaa gattgcaaaa tctgcaacga     420
gctttgggtt tactattaat ggtggagatg gatataaaa tgctcaaaaa agtaccacca     480
ctatattttc atcctaagcc aagtgtagac tctgtattga ttgttcttga acgacatcaa     540
ccattgattt caaagaagga ctacaaaaag tatcgatctt ttgttttataa gtgggtaaac     600 cgtgaatatc gtgttctttt cactaaaaac caattccgac aggctttgaa gcatgcaaat     660
gtcactaata ttaataaact atcgaaggaa caattcttt ctattttcaa tagttacaaa     720
ttgtttcact aa                                                         732

<210> SEQ ID NO 29
<211> LENGTH: 735
<212> TYPE: DNA
<213> ORGANISM: Staphylococcus aureus
<220> FEATURE:
<221> NAME/KEY: misc_feature
<223> OTHER INFORMATION: ermC

<400> SEQUENCE: 29
atgaacgaga aaaatataaa acacagtcaa aactttatta cttcaaaaca taatatagat       60
aaaataatga caaatataag attaaatgaa catgataata tctttgaaat cggctcagga     120 aagggcatt ttacccttga attagtacag aggtgtaatt tcgtaactgc cattgaaata     180
gaccataaat tatgcaaaac tacagaaaat aaacttgttg atcacgataa tttccaagtt     240
ttaaacaagg atatattgca gtttaaattt cctaaaaacc aatcctataa atatttggt     300 aatatacctt ataacataag tacggatata atacgcaaaa ttgttttga tagtatagct     360 gatgagattt atttaatcgt ggaatacgag tttgctaaaa gattattaaa tacaaaacgc     420
tcattggcat tatttttaat ggcagaagtt gatatttcta tattaagtat ggttccaaga     480
```

| gaatattttc atcctaaacc taaagtgaat agctcactta tcagattaaa tagaaaaaaa | 540 |
| tcaagaatat cacacaaaga taaacagaag tataattatt tcgttatgaa atgggttaac | 600 |
| aaagaataca agaaaatatt tacaaaaaat caatttaaca attccttaaa acatgcagga | 660 |
| attgacgatt taaacaatat tagctttgaa caattcttat ctcttttcaa tagctataaa | 720 |
| ttatttaata agtaa | 735 |

<210> SEQ ID NO 30
<211> LENGTH: 1380
<212> TYPE: DNA
<213> ORGANISM: Staphylococcus aureus
<220> FEATURE:
<221> NAME/KEY: misc_feature
<223> OTHER INFORMATION: tetK

<400> SEQUENCE: 30

| ctattcaaac tgcttttcag aacgtttaaa tacaataatc gtcaaaagac aacataaaat | 60 |
| aataaggata gccatggcta caagaatatt actatacact ccagaagaat aatttataaa | 120 |
| ttccagaact agtttacgat taatcaattg tagtgacaat aaacctccta caattgctat | 180 |
| acctgttccc tctgataaaa aacttgtgaa atttagcaaa ctcattccag aagcaacttc | 240 |
| ttcttcagaa agactacttg atactatttt tgatataact gttttagtaa aagataatcc | 300 |
| gcccataaca aatataaaca taaaagtagt caaccacata ctaaactcaa caaaaaatgc | 360 |
| aatagttaaa aaacttatag agatagacaa tgatcctaaa ataaaaacaa ataatgatcc | 420 |
| ttttctatcc actaaaaaac caccaaaata accaaaaaca ataacactca tggttccagg | 480 |
| aaaaataaca ctattaccta ttgtcgctac atttacatga taaatagttt tcatcatata | 540 |
| aggcaccatt gatataaaac cagctactat agaaaatatt agcccaccag aaaacaaacc | 600 |
| aagcataaac ggaatgtttt tccctagttt aggattaata aaagggttag aaactcttga | 660 |
| aatatgttta ataaaaatca caaaaaagat tgtgaagagt attaaaaaag tccaattata | 720 |
| atttgtcgta aataacataa aacatataat acttatagac attaaaacaa tacctacgat | 780 |
| atctaatgta ttttttgttg atttaccagg taccattact ttaataagaa aaggtatagt | 840 |
| tactattgta atcataggaa gtataagtag gtaagaccaa tgaatataat gtgctattat | 900 |
| tcccccctatt gaaggaccta acccttcacc taaagctaca attgatccta taaaaccaaa | 960 |
| ggctttgcct tgtttttttc ttgtaatatt tctagctaca accaccataa tcagtgaagg | 1020 |
| gaatgcagca gatcctactc cttgtactaa cctaccaaaa atcaaaataa aaagtgatt | 1080 |
| gtgaccaata aaagcaatca atgaaccaag acagctcaaa ctaataccaa taattaacaa | 1140 |
| ttttttttata tttatataat cagataattt tccatatact gctgttccta tcgaaaagt | 1200 |
| taacatatat gcagtgttta cccagtttgt aattccagga gtagtattaa aatgatttgc | 1260 |
| aatatcaggt aaagaaacat ttaaaaccat ttcatttaat acactaaaaa atgaaagaat | 1320 |
| acaaagccaa aataaaacgc tataaaacaa acctttaaat tttttatata aactaaacaa | 1380 |

<210> SEQ ID NO 31
<211> LENGTH: 1920
<212> TYPE: DNA
<213> ORGANISM: Staphylococcus aureus
<220> FEATURE:
<221> NAME/KEY: misc_feature
<223> OTHER INFORMATION: tetM

<400> SEQUENCE: 31

| ctaagttatt ttattgaaca tatatcttac tttatctatc cgactatttg gacgacgggt | 60 |

```
ctggcaaaca ggttcgccag tggtaacctg atatcctttt agctctgcta aacaaacact    120
aagcccattt gtaaaaaaag ttaaatcatt gcgataatct tgaatacatc gagcaggaat    180
ttctccaata ataatgacct cattattttt cagttgagta tttacgatat ttgcacaata    240
tttgggagca tcgttatatg cccgtgaaag atattcctgt ggtgcataaa ctttaaaact    300
aagatatggc tctaacaatt ctgttccagc ttttctaaag gcttgctcca gtacaatagg    360
agtaagcatc cgaaaatctg ctggagtact aacagggcta tagtataaac cgtacttaaa    420
acagatttta caatccgtca cattccaacc atataatcct tgttcgcaac catagcgtat    480
cccttccata actgcatttt gaaatgattg atttaagtat ccaagagaaa ccgagctctc    540
atactgcatt ccacttccca acggaagcgg tgatacagat aaaccaatgg aagcccagaa    600
aggatttggc ggcacttcga tgtgaatggt atattctgca tttttttaacg gtctctccat    660 ataaatgact gtaggctctt ttagttctat ctccacatga tactttctt gcaacagtgc     720 actaatcact tccatttgta ctttccctaa gaaagaaagt ataatttcat gtgtcgtaga    780
atccacgtaa tatcgtagaa gcggatcact atctgagatt tccaaaaggg catcaagcaa    840
catttctctc tgttcaggtt tactcggttc aacagttgtt tgtagtagag ggtgcggatt    900
ttcaatcttt tttctctgtg gcaatagttt tgtatctcca agaacactat ttaacttcaa    960
aaactcattt tgcaaaataa caatttctcc agaataagct ctatcaatct tacataattc   1020
accatttatt gaagtataca tttctgtaac ttttattttt tcttttctg atactctaac    1080 cgaatctcgt aaatgtagta ctccactata aaggcgtata tatgcaagac gttgtctttt   1140
ttttgtatat tcaattttga aaacatttcc gcaaagttca gacggacctc gatgtgttga   1200
tgaataaaat ttattagtaa taacttctat aaggttatca atccctatat tacttttgc    1260 acttccatga taaagaggga acagagaaca attctgaaat cttatgcttt cctcttgttc   1320
gagttccaat gcttctaatg atttaccgga catatatttc tctaaaaggt catcgtttcc   1380
ctctattacc gtatcccatt gttcagattc ggtaaagttc gtcacacaca tattaggata   1440
cagttctacc ttctgtttga ttacaatttc ggcagaaagt ttctctttaa tatcctgata   1500
aaccgttgat aaatcaattc cattttggtc aatcttattg ataaaaaaga ttgtgggaat   1560
ccccattttc ctaagtgcat gaaataatat acgagtttgt gcttgtacgc catcttttgc   1620
agaaatcagt agaattgccc catctaaaac tgataatgaa cgatatactt ctgctaagaa   1680
atccatatgt cctggcgtgt ctatgatgtt caccttcgta ttttcccact gaaaagaggt   1740
tattcctgtc tgaattgtaa ttcctctctg acgttctaaa agcgtattat ccgtcctcgt   1800
tgtacctttg tccacgcttc ctaattctgt aatcgctcca ctgttatata ataagctttc   1860
tgttaaggta gtttttcctg catcaacatg agctaaaact ccaatattaa taattttcat   1920
```